US00PP11619P

United States Patent [19]

van den Bosch

[11] Patent Number: Plant 11,619

[45] Date of Patent: Nov. 7, 2000

[54] HYPERICUM PLANT NAMED 'BOSAQUE'

[75] Inventor: Bernard Renee van den Bosch, Rijnsburg, Netherlands

[73] Assignee: H. + B. R. van den Bosch B.V., Rijnsburg, Netherlands

[21] Appl. No.: 09/250,012

[22] Filed: Feb. 12, 1999

[51] Int. Cl.[7] ..... A01H 5/00

[52] U.S. Cl. ..... Plt./226

[58] Field of Search ..... Plt./226

[56] References Cited

U.S. PATENT DOCUMENTS

P.P. 568 3/1943 Grullemans ..... Plt./226

P.P. 10,993 7/1999 van den Bosch ..... Plt./226

P.P. 10,994 7/1999 van den Bosch ..... Plt./226

*Primary Examiner*—Howard J. Locker

*Assistant Examiner*—Kent L. Bell

*Attorney, Agent, or Firm*—C. A. Whealy

[57] ABSTRACT

A distinct cultivar of Hypericum plant named 'Bosaque', characterized by its very early flowering, plants flower about 12 weeks after planting; medium stem length, typically about 55 cm; small reddish purple berries; and excellent postproduction longevity, cut stems typically last about 16 days.

1 Drawing Sheet

BACKGROUND OF THE INVENTION

The present invention relates to a new and distinct cultivar of Hypericum plant, botanically known as *Hypericum androsaemum*, commonly referred to as Saint John's Wort, commercially used as a cut flower, and hereinafter referred to by the cultivar name 'Bosaque'. To date, the new Hypericum has not been noted to have any medicinal value.

The new Hypericum is a product of a planned breeding program conducted by the Inventor in Rijnsburg, The Netherlands. The objective of the breeding program was to develop cut Hypericum varieties with attractive berry color, early flowering, long flowering stem length, and large berry size. The new cultivar originated from a cross made by the Inventor in 1988 of two proprietary seedlings. The proprietary selection code number 83 was the female, or seed, parent, and the proprietary selection code number 75 was the male, or pollen, parent.

The cultivar 'Bosaque' was discovered and selected by the Inventor in August, 1989 as a flowering plant within the progeny of the stated cross in a controlled environment in Rijnsburg, The Netherlands.

Asexual propagation of the new Hypericum by cuttings taken at Rijnsburg, The Netherlands, has shown that the unique features of this new Hypericum plant are stable and reproduced true to type in successive generations.

SUMMARY OF THE INVENTION

The following traits have been repeatedly observed and are determined to be the unique characteristics of 'Bosaque'. These characteristics in combination distinguish the new Hypericum plant as a new and distinct cultivar:

1. Very early flowering; plants flower about 12 weeks after planting.

2. Medium stem length; typically about 55 cm.

3. Small reddish purple berries.

4. Excellent postproduction longevity; cut stems typically last about 16 days.

The new Hypericum can be compared to the cultivar 'Dual Flair', disclosed in U.S. Plant Pat. No. 10,979. In side-by-side comparisons conducted in Rijnsburg, The Netherlands, plants of the new Hypericum flower earlier, are taller, have smaller leaves, and berries are more red in color than plants of the cultivar 'Dual Flair'.

Plants of the new Hypericum have not been observed under all possible environmental conditions. The phenotype may vary significantly with variations in environment such as temperature, light or fertility level, without, however, any variance in genotype.

BRIEF DESCRIPTION OF PHOTOGRAPHS

The accompanying colored photographs illustrate the new Hypericum plant, showing the colors as true as it is reasonably possible to obtain in colored reproductions of this type.

The photograph at the top of the sheet comprises a side perspective view of typical plants with berries of the new Hypericum under outdoor commercial production.

The photograph at the bottom of the sheet comprises a close-up view of typical leaves, berries and flowers of plants of the new Hypericum. Flower, fruit and foliage color in these photographs may appear different from the actual colors due to light reflectance.

DETAILED BOTANICAL DESCRIPTION

The following observations, measurements, values, and comparisons describe plants grown in Rijnsburg, The Netherlands, under outdoor commercial production practice. In the following description, color references are made to The Royal Horticultural Society Colour Chart except where general terms of ordinary dictionary significance are used.

Classification:

*Botanical.*—*Hypericum androsaemum* cultivar 'Bosaque'.

*Commercial.*—Cut Hypericum; To date, no medicinal value.

Parentage:

*Female parent.*—Proprietary *Hypericum androsaemum* selection code number 83.

*Male parent.*—Proprietary *Hypericum androsaemum* selection code number 75.

Propagation:

*Type.*—Cuttings.

*Rooting habit.*—Fine fibrous and well-branched.

Plant description:

*Form.*—Upright and broad woody shrub with erect lateral branches, branch angle about 40°.

*Growth habit.*—Moderately vigorous. Freely branching and dense growth.

*Plant height.*—About 55 cm.

*Stem and lateral branch color.*—Red-brown anthocyanic coloring.

*Foliage description.*—Leaves arranged oppositely, single, sessile, and generally symmetrical. Length: About 7 cm. Width: About 4 cm. Shape: Ovate with acute apex and obtuse base. Margin: Entire. Texture: Smooth, leathery. Color: Upper side: Dark green, 137A to 137B. Under side: Light green, 137B.

Flower description: P2 *Flower type and habit.*—Large golden yellow flowers arranged in apical compound umbels. Very early flowering; plants flower about 12 weeks after planting. Natural flowering season in The Netherlands is early autumn, typically August and September. Flowers not fragrant.

*Postproduction longevity.*—Cut flowers are typically harvested when all flowers have developed berries. From flowers to berries takes about three weeks. Postproduction longevity of cut stems of the new Hypericum typically is about 16 days.

*Flower diameter.*—About 2.4 to 3 cm.

*Petals.*—Quantity: Typically five per flower. Length: About 1.3 cm. Width: About 9 mm. Shape: Elliptic, obtusely rounded, slightly asymmetrical. Margin: Entire. Orientation: Concave and slightly bent back. Color, both surfaces: 14A to 14B.

*Sepals.*—Quantity: Typically five per flower; three larger sepals and two smaller sepals. Shape: Broadly elliptic with nearly rounded apex, often slightly asymmetrical. Orientation: Inner angle of about 70° to peduncle. Color: Upper side: Green, 142A, with brown-red anthocyanic shading, especially at apex. Under side: Green, 137B, with red anthocyanic nerves, especially at base.

*Peduncles.*—Strength: Strong. Aspect: Erect. Length: About 1.5 to 2 cm. Color: Green with brown-red anthocyanic color, 176A to 178A to 181A.

*Reproductive organs.*—Stamens: Stamen shape: Slightly fan-shaped. Stamen color: Yellow. Anther color: Dark yellow. Pollen: Present. Pistils: Style quantity: Three per flower. Style color: Yellow-green. Stigma color: Reddish brown. Ovary color: Pale greenish yellow.

*Fruit description.*—Type: Capsule, pyxis. Shape: Oval. Length: About 1 cm. Diameter: About 9 mm. Color: Slightly more red than 185A to 185B.

Disease resistance: Resistance to pathogens common to Hypericum has not been observed under commercial production conditions.

It is claimed:

1. A new and distinct Hypericum plant named 'Bosaque', as illustrated and described.

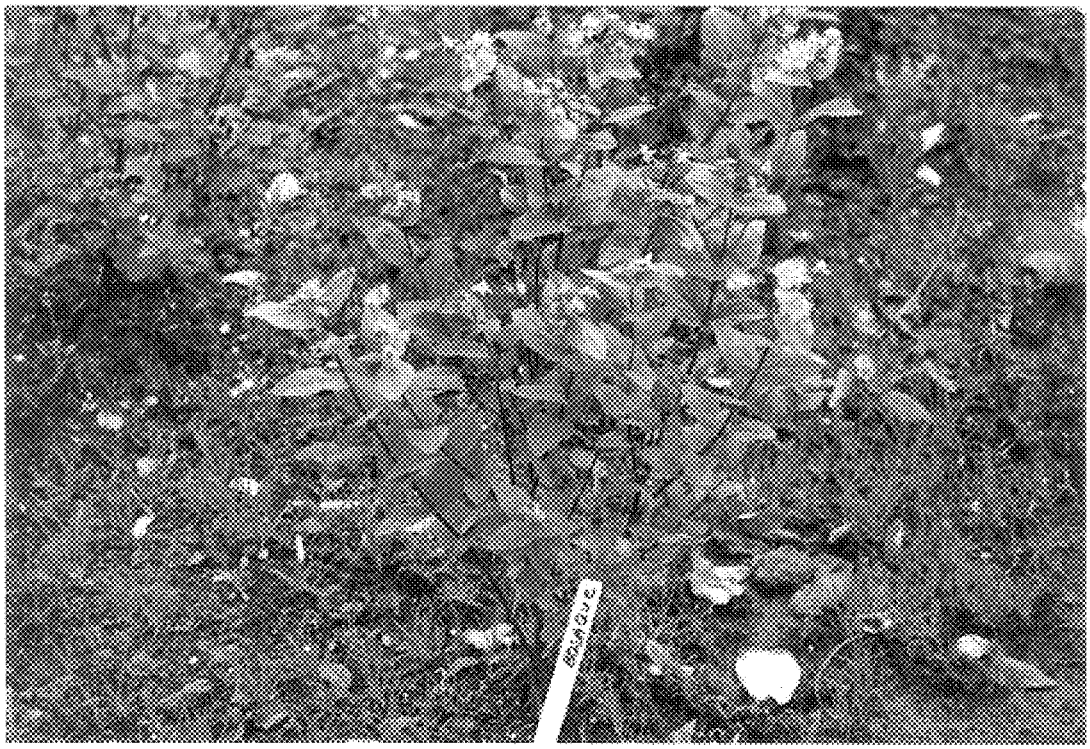
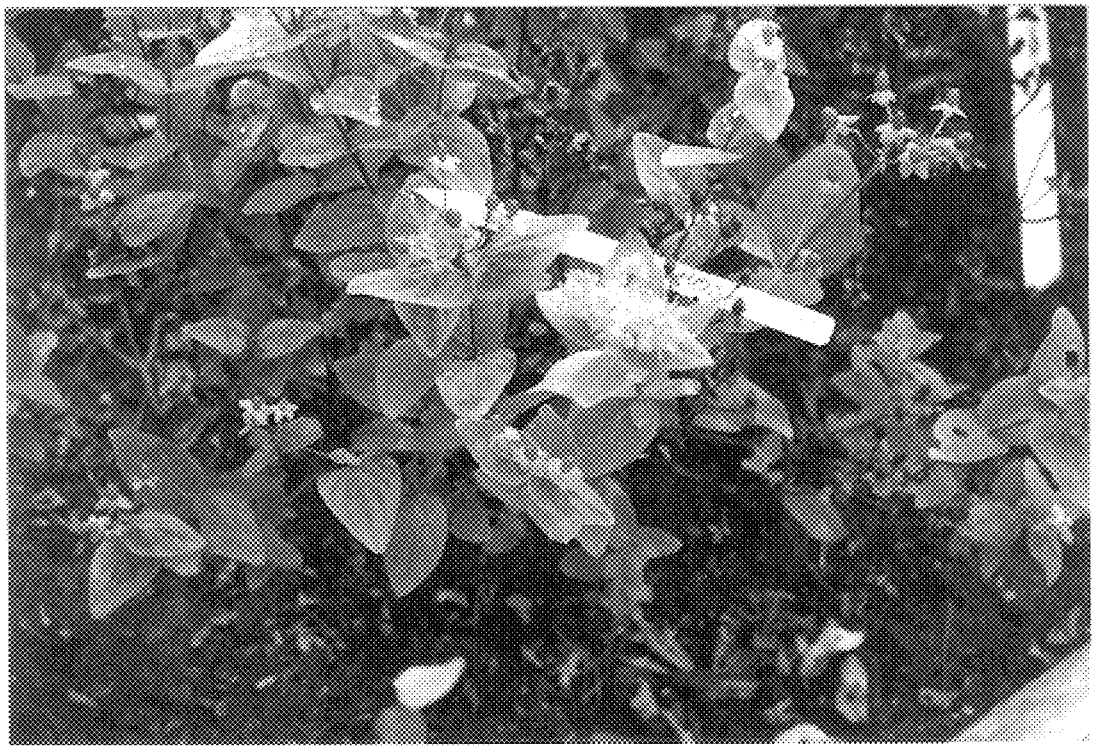

* * * * *